United States Patent
Sarr

(10) Patent No.: US 7,823,451 B2
(45) Date of Patent: Nov. 2, 2010

(54) PULSE ECHO/THROUGH TRANSMISSION ULTRASONIC TESTING

(75) Inventor: Dennis P. Sarr, Kent, WA (US)

(73) Assignee: The Boeing Company, Chicago, IL (US)

(*) Notice: Subject to any disclaimer, the term of this patent is extended or adjusted under 35 U.S.C. 154(b) by 267 days.

(21) Appl. No.: 12/115,960

(22) Filed: May 6, 2008

(65) Prior Publication Data

US 2009/0277269 A1   Nov. 12, 2009

(51) Int. Cl.
G01N 29/06 (2006.01)
G01N 29/275 (2006.01)

(52) U.S. Cl. ............................. 73/598; 73/623; 73/624

(58) Field of Classification Search ............. 73/597, 73/598, 618, 620, 623, 624
See application file for complete search history.

(56) References Cited

U.S. PATENT DOCUMENTS

| | | | |
|---|---|---|---|
| 6,032,534 A * | 3/2000 | Sherwin | ........................ 73/628 |
| 6,722,202 B1 | 4/2004 | Kennedy et al. | |
| 7,228,741 B2 | 6/2007 | Georgeson et al. | |
| 7,249,512 B2 | 7/2007 | Kennedy et al. | |
| 7,263,889 B2 | 9/2007 | Kennedy et al. | |
| 2006/0162456 A1 * | 7/2006 | Kennedy et al. | ............... 73/620 |
| 2007/0144260 A1 * | 6/2007 | Fei et al. | ........................ 73/596 |

OTHER PUBLICATIONS

J.E. Michaels et al., "Self-Calibrating Ultrasonic Methods for In-Situ Monitoring of Fatigue Crack Progression" Review of Quantitative Nondestructive Evaluation, vol. 24, American Inst. of Physics, 0-7354-0245-0/05 (2005).

T.E. Michaels, "Application of Acoustic Wavefield Imaging to non-contact ultrasonic inspection of bonded components" Review of Quantitative Nondestructive Evaluation, vol. 25, American Inst. of Physics, 0-7354-0312-0/06 (2006).

* cited by examiner

*Primary Examiner*—Hezron Williams
*Assistant Examiner*—Rose M Miller

(57) ABSTRACT

Ultrasonic testing on a part includes scanning the part while performing pulse echo and through transmission ultrasonic testing on the part; converting pulse echo data into time of flight (TOF) and amplitude channels, and converting through transmission data into a data representation that identifies porosity. The testing further includes analyzing the pulse echo TOF to identify locations of any anomalies in the part, and using loss of back (LOB) at each of the identified locations to discriminate low porosity from other anomalies.

22 Claims, 6 Drawing Sheets

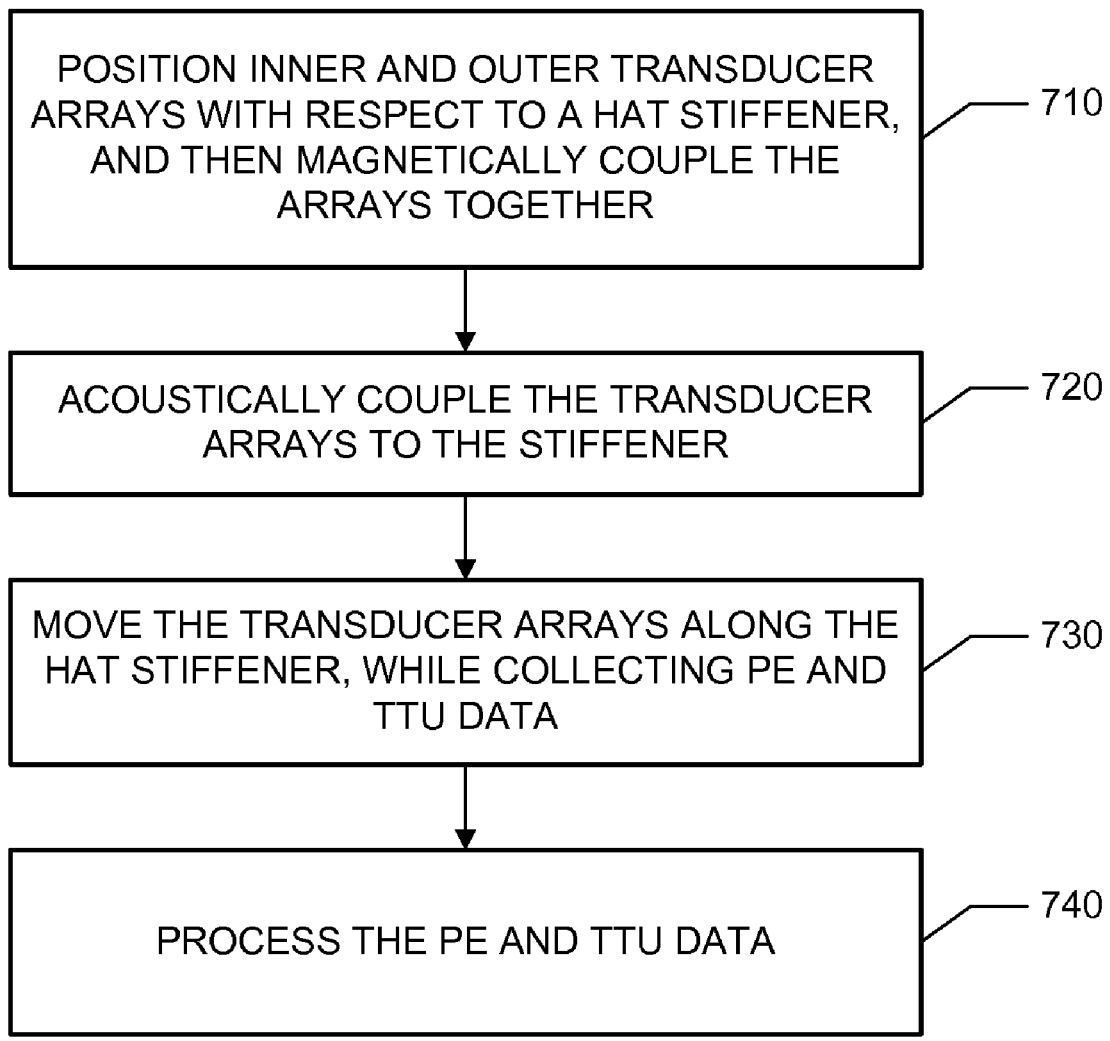

PULSE ECHO/THROUGH TRANSMISSION ULTRASONIC TESTING

BACKGROUND

Nondestructive inspection (NDI) of a structure involves thoroughly examining the structure without harming it or significantly disassembling it. Nondestructive inspection is commonly used in the aircraft industry to validate the health (e.g., integrity and fitness) of aircraft structures.

Consider the construction of commercial aircraft having fuselage stiffeners made of composite material. NDI is performed on each stiffener. However, given the number of features to test on each stiffener, the length of each stiffener, the number of stiffeners in the aircraft, and the number of aircraft being manufactured at any given time, there might be miles of stiffener to inspect.

Fast, comprehensive NDI of these stiffeners is needed.

SUMMARY

According to an embodiment herein, ultrasonic testing on a part includes scanning the part while performing pulse echo and through transmission ultrasonic testing on the part, converting pulse echo data into time of flight (TOF) and amplitude channels, and converting through transmission data into a data representation that identifies porosity. The testing further includes analyzing the pulse echo TOF to identify locations of any anomalies in the part, and using loss of back (LOB) at each of the identified locations to discriminate low porosity from other anomalies.

According to another embodiment herein, a method of performing nondestructive inspection of a composite hat stiffener includes positioning an outer transducer array along a cap and upper radius of the hat stiffener, and an inner transducer array having a trapezoidal configuration of transducers inside the hat stiffener. The method further includes scanning the transducer arrays along the hat stiffener while obtaining pulse echo and through transmission data about the cap and the upper radius of the hat stiffener. Obtaining the pulse echo data for the cap and upper radius includes using the outer transducer array to generate acoustic signals and detect reflections of the signals. Obtaining the through transmission data for the cap and the upper radius includes using the inner transducer array to generate acoustic signals and the outer transducer array to detect those signals transmitted through the cap and the radius.

According to another embodiment herein, apparatus for performing ultrasonic testing on an aircraft fuselage stiffener includes an outer transducer array operable in pulse echo and through transmission modes for scanning a cap and radius of the hat stiffener, and an inner transducer array having a trapezoidal configuration of transducers operable in through transmission mode for scanning an inner surface of the hat stiffener. The transducer arrays cooperate to perform both pulse echo and through transmission ultrasonic testing on the fuselage stiffener.

BRIEF DESCRIPTION OF THE DRAWINGS

FIG. 7 is an illustration of a method of using the inner and outer transducer arrays to perform pulse echo and through transmission ultrasonic testing on a fuselage stiffener.

DETAILED DESCRIPTION

Figure 1:
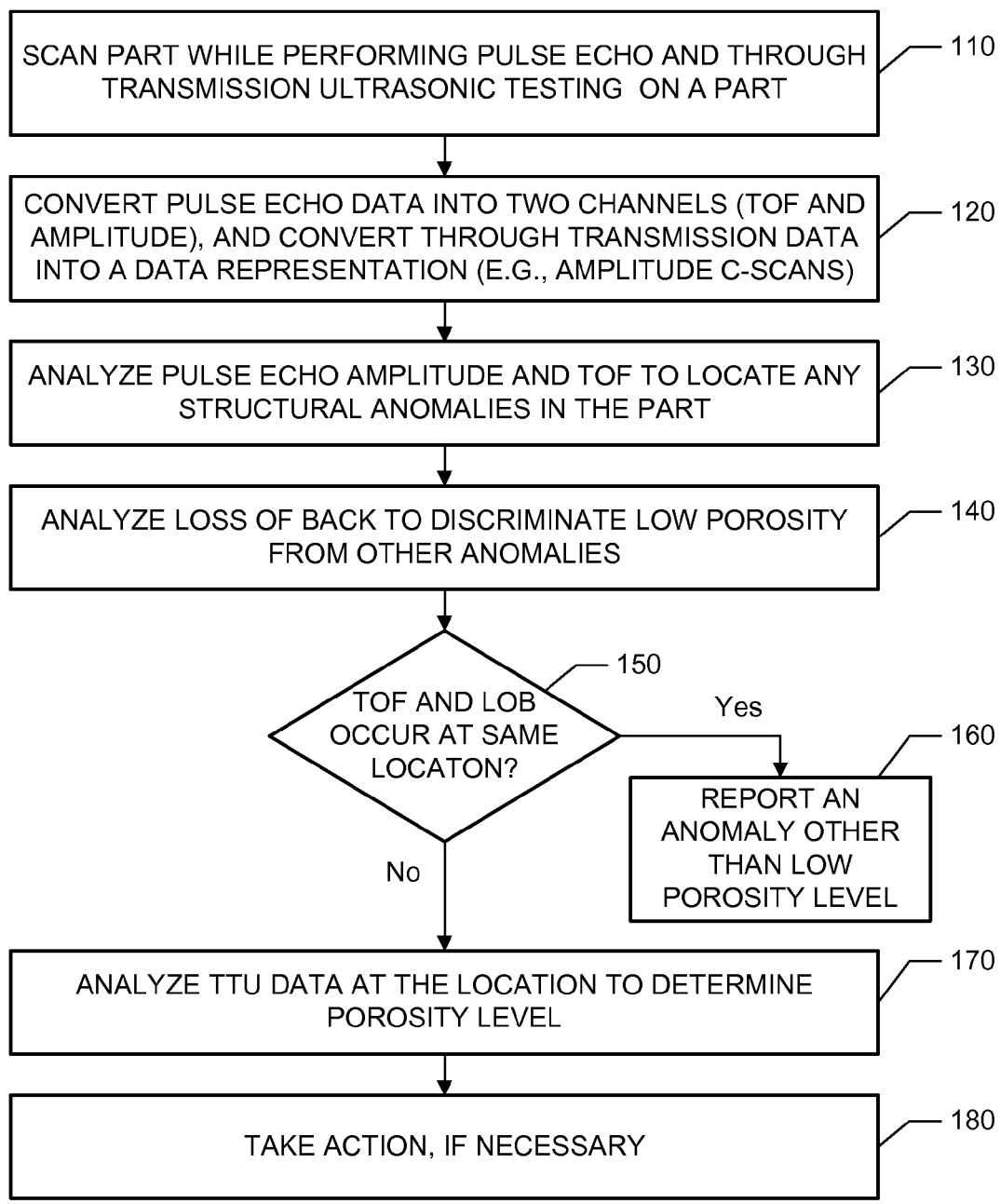
FIG. 1 is an illustration of a method of performing pulse echo and through transmission ultrasonic testing on a part.

Reference is made to FIG. 1, which illustrates a method of performing ultrasonic testing on a part. The testing is performed with first and second probes. The first probe is operable in pulse echo mode to generate sound pulses that are transmitted through a front surface of the part, and measure reflected acoustic energy that reaches the front surface. The first and second probes are also operable in through transmission mode to generate sound pulses that are transmitted through one surface of the part and measure acoustic energy at the opposing surface of the part.

At block 110, the part is scanned while pulse echo and through transmission testing are performed. The first probe is scanned along the front surface of the part, and the second probe is scanned along the back surface of the part. As the probes are being slid, pulse echo (PE) data and through transmission ultrasonic (TTU) data are being acquired simultaneously. In the alternative, the PE and TTU data may be obtained sequentially. The first probe is operated in pulse echo mode to obtain the PE data. The first and second probes are also operable in through transmission mode to obtain the TTU data.

The probes may have multiple time gates. A time gate refers a window of analysis in time and amplitude. Gates are typically used to filter out data from wedges, front surfaces, etc. A time gate for pulse echo is usually set to find reflections within the part, after the front surface of the part. For TTU, the time gate is set across the entire part. A gate could be adjusted to look at a specific part of the reflection, for example at a flange bondline, to determine whether an anomaly is at one particular depth or whether it is not an anomaly but rather a feature of the part.

At block 120, PE data is processed into two channels: time of flight (TOF) and amplitude. TOF may use a gate at either the peak value or the first crossing of the signal "higher" in amplitude of the gate threshold (usually in percentage of screen height).

Also at block 120, the TTU data is converted into a data representation that indicates porosity level of the material. A common data representation is a C scan.

At block 130, the pulse echo data is analyzed to locate structural anomalies in the part. The amplitude information indicates whether an anomaly is present. For example, a large reflection, say greater than 40% amplitude, with a linear TCG, will occur in time before the back wall, indicating a delamination, foreign material, or another anomaly. The TOF information represents the location of the anomaly within the material, that is, how far from the surface the anomaly is located.

At block 140, loss of back (LOB) is analyzed at each identified location to discriminate low porosity from other anomalies, such as delamination, disband, or foreign material within the part. For example, LOB may use a gate on the back wall reflection. The LOB may be compared to a threshold such as an 80% level, using Time Corrected Gain (TCG) or Distance Amplitude Correction (DAC). If LOB goes below 20%, for example, it is said that LOB occurred. If TOF and LOB occur at the same location of the part (block 150), an anomaly other than low porosity level is reported at that location (block 160). Thus, the LOB is used to distinguish low porosity from other anomalies.

If the anomaly is identified as low porosity (block 150), the TTU C-scan of the location is analyzed to determine porosity level (block 170). TTU measures porosity levels with better accuracy and dynamic range than pulse echo. Pulse echo testing typically measures porosity level up to 2%. A TTU C-scan can accurately indicate higher porosity levels (e.g., 8%).

At block 180, an action is taken, if necessary. If the measured porosity level is below a threshold of, say, 2%, then no action is taken. If the measured porosity level is above the threshold T (block 180), then low porosity is reported and an action is taken. For example, the low porosity material in the part can be repaired.

Having a system that can accurately measure 4% or 6% or 8% may mean the part can be used without any repair process. Even if the part is repaired, the repaired material will still usually have 2 or 3% porosity. Thus, measuring the porosity level with greater accuracy can avoid unnecessary repair. This can save a lot of rework or prevent repair work that does not improve the part.

Providing PE and TTU data for the same location provides greater capability for detecting porosity due to the approximate doubling of the dynamic range of the UT system.

The two PE gates amplitude and TOF along with the TTU amplitude at the same spot provides much information in a C-scan image. Also C-scan data continuity, and overlap with PE data is desirable as it decreases the time needed to detail an anomaly and reduces error that is inherent in separate scans (due, for example, to an inaccurate starting point for a second scan, repeatability of a robot, gantry or crawler during a second scan, etc.).

Together, the TTU and PE testing provide comprehensive NDI for foreign materials, delamination and porosity. These two types of tests complement each other. The pulse echo testing satisfies more stringent testing requirements than TTU testing. TTU testing alone would provide the necessary void and porosity but not necessarily all the foreign material (type 1 and 2) detection capabilities. The PE provides such foreign material detection capabilities. However, TTU testing is more accurate and provides analysis for higher porosity levels.

Figure 2:
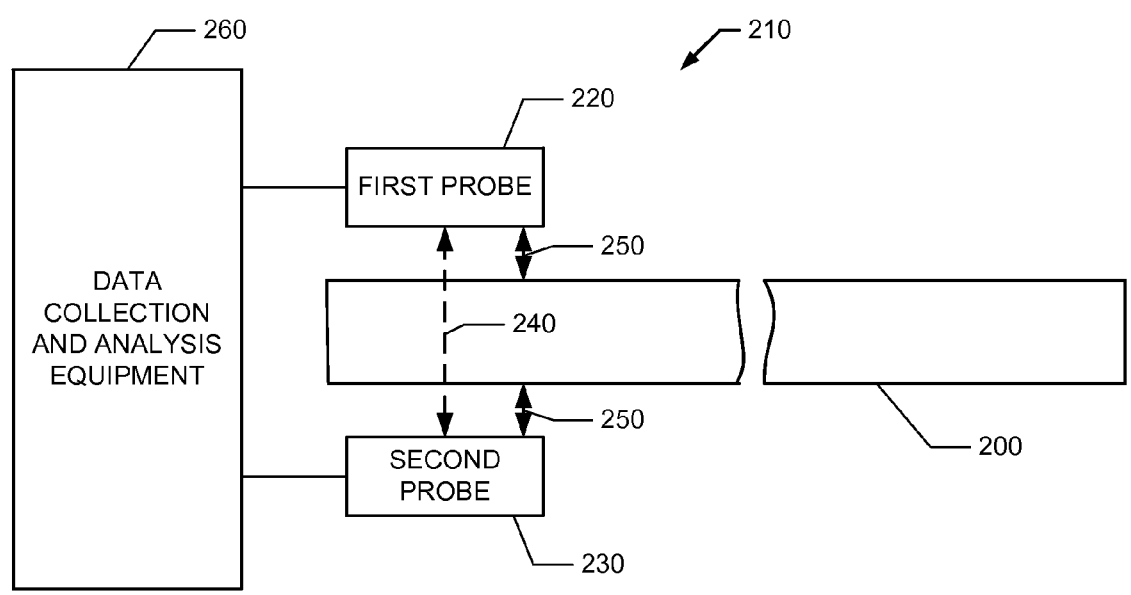
FIG. 2 is an illustration of a system for performing pulse echo and through transmission ultrasonic testing on a part.

Reference is now made to FIG. 2, which illustrates a system 210 for performing PE/TTU testing on a part 200. The system 210 includes a first probe 220 for performing PE testing at a front surface of the part 200, and a second probe 230 that cooperates with the first probe 220 to perform through transmission testing of the part 200. The system 210 further includes means 240 for providing magnetic coupling between the two probes 220 and 230 so the two probes 220 and 230 remain aligned during scanning. The system 210 also includes means 250 for providing acoustic coupling between the part 200 and each probe 220 and 230.

During ultrasonic testing, one probe generates a sound beam that travels thru the acoustic coupling material (typically water) where it hits the surface of the part. The main beam enters the surface into the part and hits the back wall. The longitudinal wave of the sound beam is mainly used, so if perpendicular to the back wall, there will be a reflected sound wave off the back wall as well as a sound wave that goes thru the back wall. The impedance of the materials determine the amount of the signal that is reflected and transmitted, The reflected signal returns to the origination transducer, and the transmitted signal continues to the other probe of the system 210, which functions as a TTU second transducer. The ultrasonic testing system 210 may have to have the capability of capturing both signals simultaneously or use two pulses sequentially and sharing the system's electronics.

The system 210 further includes equipment 260 such as a computer for collecting the PE and TTU data from the probes and processing the data to locate anomalies and regions having high porosity. The PE and TTU data may be processed offline.

The PE/TTU testing is not limited to a part having any particular composition or structure. However, the PE/TTU testing is especially useful for testing hybrid parts such as parts made of different materials (e.g., composites) and solid laminates with honeycomb-core structures.

The PE/TTU testing is not limited to any particular type of part. However, it is especially advantageous for performing comprehensive, yet relatively fast testing of aircraft fuselage stiffeners made of composite material.

Figure 3:
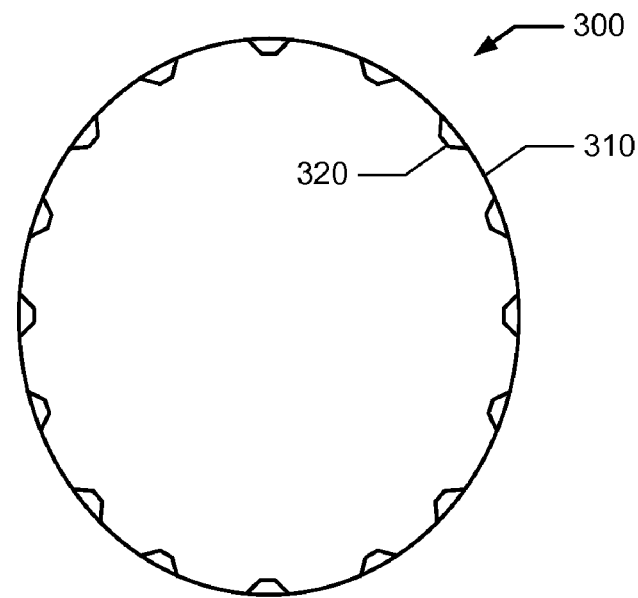
FIG. 3 is an illustration of a portion of an aircraft fuselage.

Reference is made to FIG. 3, which illustrates a portion of an aircraft fuselage 300. The fuselage 300 includes skin 310 and a plurality of fuselage stiffeners 320 disposed about the skin 310. The fuselage stiffeners 320 increase the stiffness of the skin 310. The skin 310 and the fuselage stiffeners 320 may be made of a composite such as carbon fiber reinforced plastic (CFRP), However, the skin 310 and the fuselage stiffeners 320 are not limited to any particular composition. The composition could include a metal such as aluminum, titanium, or alloys thereof.

The number of fuselage stiffeners 320 shown in FIG. 3 is for illustrative purposes only. The number of fuselage stiffeners 320 in a fuselage 300 will be aircraft-specific. For example, certain large commercial aircraft could have about eighty fuselage stiffeners 320 per barrel.

Figure 4:
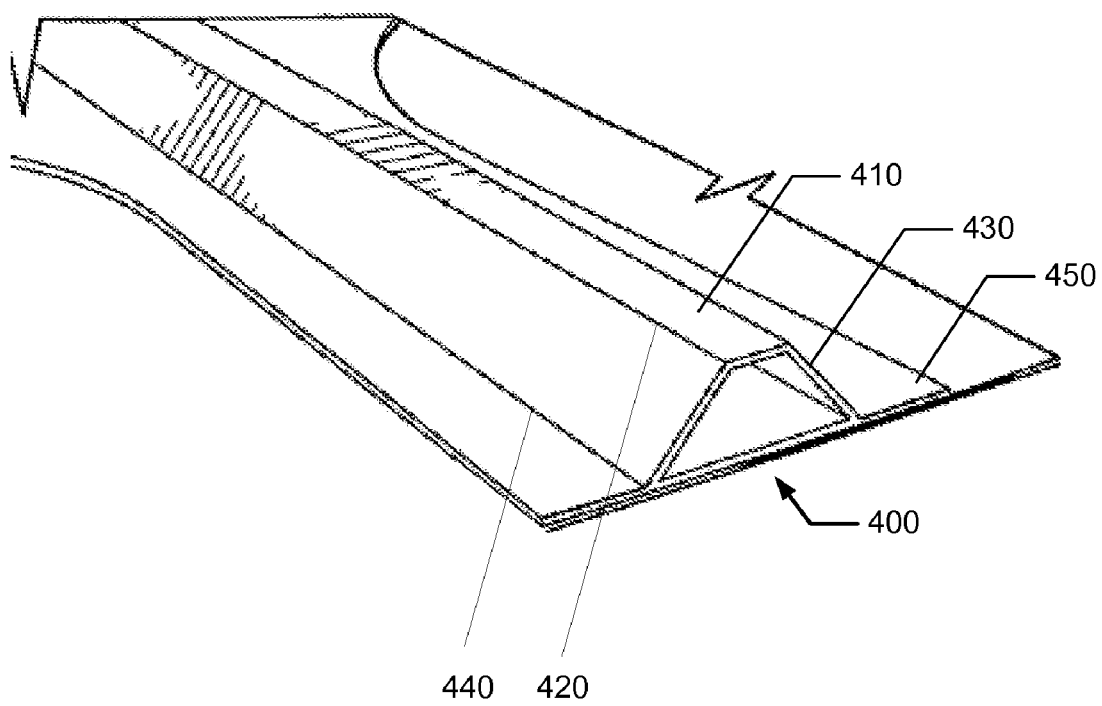
FIG. 4 is an illustration of a fuselage stiffener.

Additional reference is made to FIG. 4, which illustrates a certain type of fuselage stiffener that will be referred to as a "hat stiffener" 400. The hat stiffener 400 includes a cap 410, upper radii 420, upper webs 430, lower radii 440, and lower webs 450. These features 410-450 give the hat stiffener 400 a trapezoidal cross-section.

Comprehensive testing of a hat stiffener 400 would include PE/TTU testing of the cap 410 and upper radii 420, and conventional PE testing of the webs and lower radii 430-450.

Figure 5:
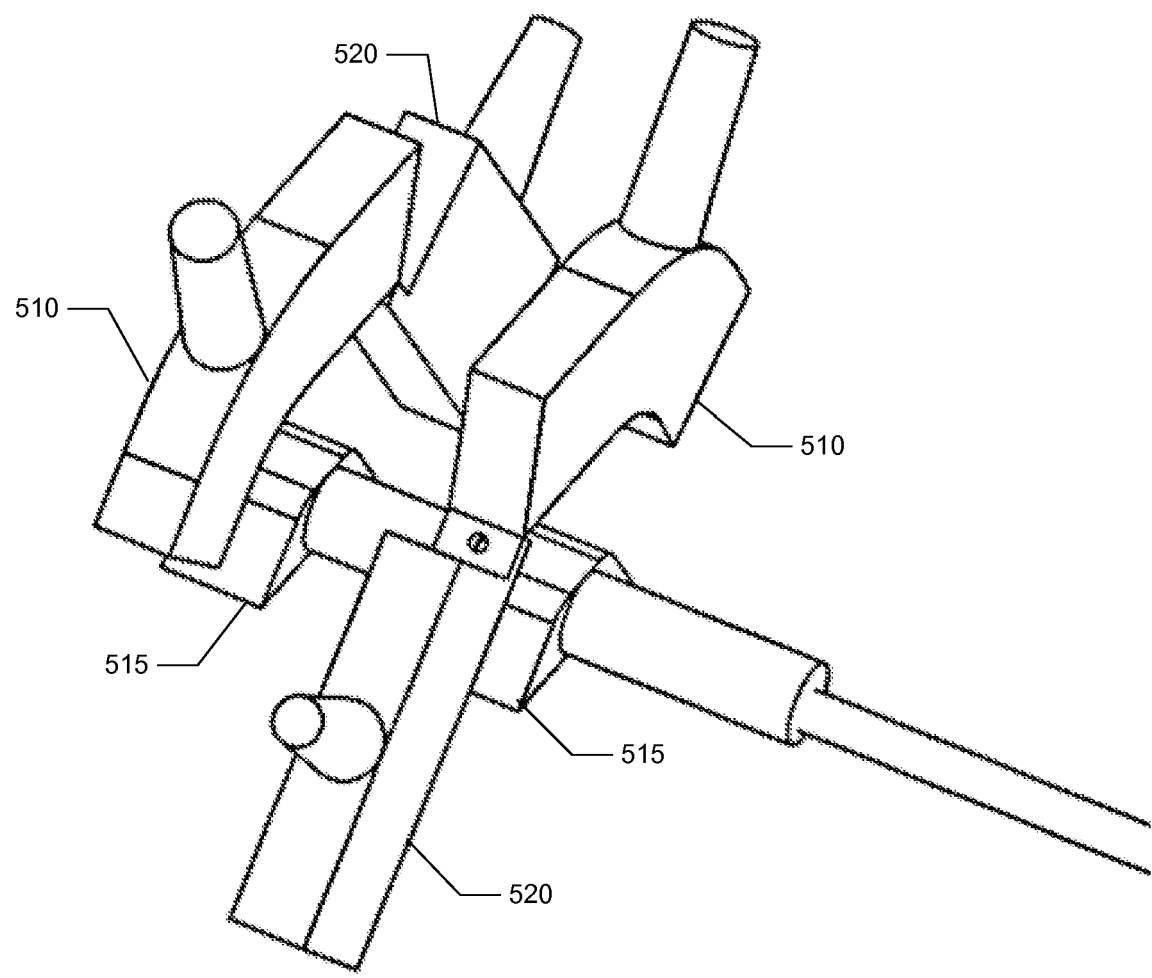
FIG. 5 is an illustration of inner and outer transducer arrays for performing ultrasonic testing on a fuselage stiffener.

Reference is now made to FIG. 5, which illustrates two groups of transducer arrays for performing comprehensive ultrasonic testing of a hat stiffener 400. The front group inspects the cap 410 and one side (one upper radius 420, one upper web 430, and one lower radius 440) of the hat stiffener 400. The back group inspects the cap 410 and the other side 420-440 of the hat stiffener 400. Each group includes an outer transducer array 510 and an inner transducer array 515 for performing PE/TTU testing of the cap 410 and one upper radius 420. Each outer transducer array 510 includes a combination of linear and curved arrays so the cap 410 and upper radius 420 can be inspected at the same time. However, the cap 410 may be inspected twice to help in the alignment of the C-scan data when needed.

Each inner transducer array 515 has a trapezoidal configuration of transducers. The inner transducer arrays 515 are held at an axial sound alignment (for TTU) when travelling on the inner mold line surface of the hat stiffener 400.

The inner transducer arrays 515 may be designed to allow expansion of inspecting the entire cap 410 and radius 420 at one time. These arrays 515 of transducers can be customized to beam steer the UT signal if necessary.

Each group further includes a second outer transducer array 520 for performing PE testing of the webs and lower radius 430-450 on one side of the hat stiffener 400. Each second outer array 520 may include a linear array design configuration having individual arrays of discrete transducers.

Figure 6:
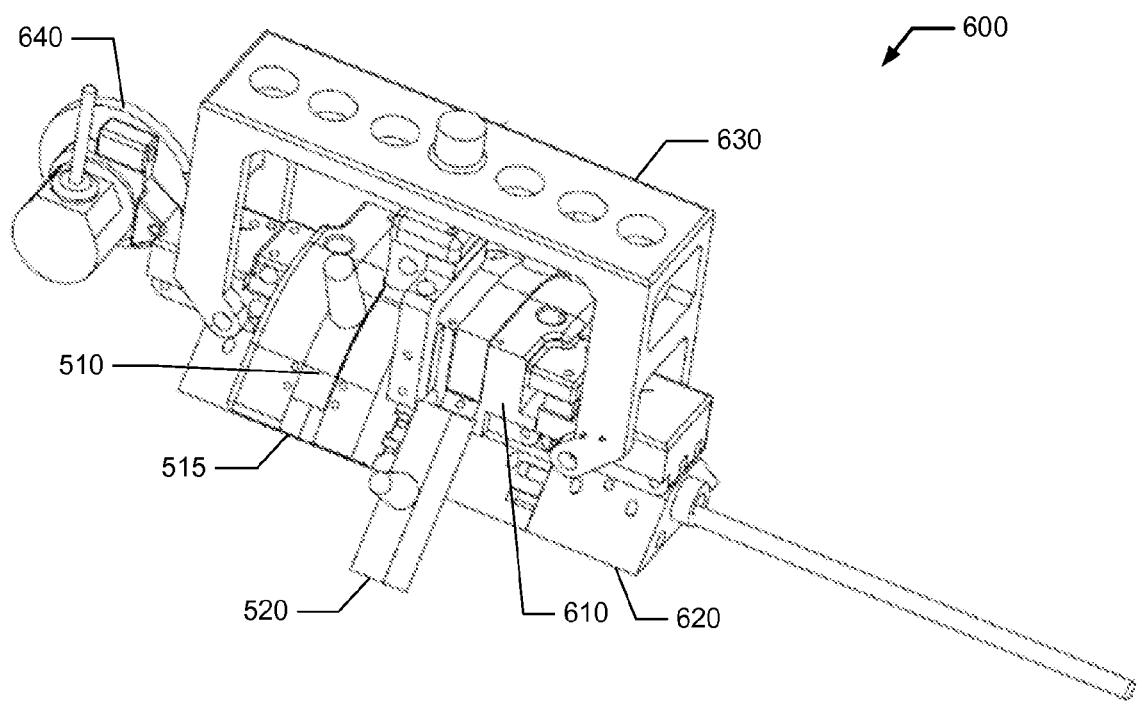
FIG. 6 is an illustration of an apparatus for performing ultrasonic testing on a fuselage stiffener.

Additional reference is made to FIG. 6, which illustrates an apparatus 600 including the transducer arrays 510, 515, and 520. The outer and inner arrays 510 and 515 may be supported by separate shoes 610 and 620.

The apparatus 600 further includes a housing assembly 630. The housing assembly 630 has the connection to the shoes 620 and to a gantry, robot or other scanning mechanism.

The housing assembly 630 may include magnets (not shown) for coupling the outer transducer arrays 510 to their corresponding inner transducer arrays 515 so they stay aligned during ultrasonic testing. For an example of magnetic coupling, see the assignee's U.S. Publication No. 20060055396 ("Alignment compensator for magnetically attracted inspecting apparatus and method"), which uses permanent magnets or electromagnets and an alignment sensor to align probes on opposite sides of a part under test.

The apparatus 600 further includes means for recording position of the transducer arrays during scanning. For example, the means could include an optical encoder 640.

The apparatus 600 may also include means (not shown) for acoustically coupling and guiding the UT signal to the transducer arrays. Such means could include a water path.

Reference is now made to FIG. 7, which illustrates a method of using the inner and transducer arrays. At block 710, the transducer arrays are positioned with respect to a hat stiffener, and then magnetically coupled together. At block 720, water is flowed through the stiffener (and through the probes) to acoustically couple the transducer arrays to the hat stiffener.

At block 730, the transducer arrays are moved along the hat stiffener, while collecting PE and TTU data. For TTU data, the inner probe generates an acoustic signal and the outer probe receives the transmitted signal. For the PE data, the outer probe generates an acoustic signal, and also receives reflections of the acoustic signal.

While the transducer arrays are being scanned, position information of the transducer arrays is made available. In some embodiments, an encoder may record position of the transducer arrays as they are being moved along the stiffener. In other embodiments that use a gantry or other robotic system to move the probes, the robotic system may provide the position information.

At block 740, the TTU and PE data is processed. The processing may be performed in real time as the data is being collected, or it may be performed off line.

The hat stiffeners may be inspected at different stages of aircraft construction. As a first example, the hat stiffeners may be inspected after they have been fastened to (e.g., co-cured with) the skin. For instance, the inspection could be performed on a fuselage barrel after it comes out of the autoclave, but before it is removed from the fabrication assembly fixture [s]. The inspection is performed before any frames and beams are added. Thus, the method may be performed by the supplier of the barrel section.

As a second example, the hat stiffeners may be inspected before they are fastened to the skin. The probes may be moved along the stiffener by a feed through system, or probes could be attached to a scanning table.

The invention claimed is:

1. A method of performing ultrasonic testing on a part, the method comprising:
scanning the part while performing pulse echo and through transmission ultrasonic testing on the part;
converting pulse echo data into time of flight (TOF) and amplitude channels, and converting through transmission data into a data representation that identifies porosity level;
analyzing the pulse echo TOF to identify locations of any anomalies in the part; and
determining loss of back (LOB) at each of the identified locations to discriminate low porosity from other anomalies.

2. The method of claim 1, further comprising reporting those locations having TOF and LOB as anomalies other than lower low porosity.

3. The method of claim 1, wherein further comprising analyzing those locations having TOF but no LOB for low porosity level.

4. The method of claim 3, wherein the part is not repaired for low porosity at a location if the porosity level at that location is below a threshold.

5. The method of claim 1, further comprising converting the through transmission data into amplitude C-scan data.

6. The method of claim 5, wherein the C-scan data has continuity and overlap with the pulse echo data.

7. The method of claim 1, further comprising optimizing dynamic range of the through transmission testing for porosity.

8. The method of claim 1, wherein the pulse echo and through transmission data are obtained simultaneously.

9. The method of claim 1, wherein the part is a hat stiffener, and wherein the pulse echo and through transmission testing are performed only on a cap and upper radius of the hat stiffener.

10. A system for performing ultrasonic testing on a part, the system comprising
a first transducer array corresponding to a front surface of the part;
a second transducer array corresponding to a back surface of the part; and
a computer programmed to control the first transducer array to perform pulse echo testing on the part, including controlling the first transducer array to generate first acoustic signals and detect reflections of the first signals, wherein the computer forms pulse echo data from the pulse echo testing and converts the pulse echo data into time of flight (TOF) and amplitude data;
the computer further programmed to control the first and second transducer arrays to perform through transmission testing on the part to form through transmission data from the through transmission testing in order to form loss of back (LOB) data; and
the computer further programmed to analyze the pulse echo TOF and amplitude data to identify locations of any anomalies in the part and to use the loss of back from the through transmission data at each of the identified locations to discriminate low porosity from other anomalies.

11. The system of claim 10, wherein the part is a hat stiffener; wherein the second transducer array has a trapezoidal shape and is located inside the hat stiffener during ultrasonic testing.

12. The system of claim 10, wherein if TOF and LOB occur at a location, the computer reports an anomaly other than low porosity level at that location.

13. The system of claim 10, wherein the computer is programmed to convert the through transmission data into amplitude C-scan data.

14. The system of claim 13, wherein the C-scan data has continuity and overlap with the pulse echo data.

15. The system of claim 10, wherein the pulse echo and through transmission data are obtained simultaneously.

16. The system of claim 10, wherein the part is a hat stiffener, and wherein the pulse echo and through transmission testing are performed only on a cap and upper radius of the hat stiffener.

17. A method of performing nondestructive inspection of a composite hat stiffener, the method comprising:
positioning a first outer transducer array along an outer surface of a cap and upper radius of the hat stiffener, and positioning an inner transducer array having a trapezoidal configuration of transducers inside the hat stiffener along, an inner surface of the cap and upper radius;
positioning a second outer transducer array along a web and lower radius of the hat stiffener; and
scanning the transducer arrays along the hat stiffener while obtaining pulse echo and through transmission data about the cap and the upper radius of the hat stiffener and obtaining pulse echo data about the web and lower radius of the hat stiffener;
wherein obtaining the pulse echo data for the cap and upper radius includes using the first outer transducer array to generate acoustic signals and detect reflections of the signals; and
wherein obtaining the through transmission data for the cap and the upper radius includes using the inner transducer array to generate acoustic signals and the first outer transducer array to detect those signals transmitted through the cap and the radius.

18. The method of claim 17, wherein the outer and inner transducer arrays constitute a first group for scanning the cap and an upper radius on one side of the hat stiffener; and wherein a second group of outer and inner transducer arrays is used to scan the cap and an upper radius on another side of the hat stiffener.

19. Apparatus for performing ultrasonic testing on an aircraft fuselage hat stiffener, the apparatus comprising:
a first outer transducer array operable in pulse echo and through transmission modes for scanning a cap and upper radius of the hat stiffener;
a second outer transducer for scanning a web and lower radius of the hat stiffener; and
an inner transducer array operable in through transmission mode for scanning an inner surface of the hat stiffener;
the inner and first outer transducer arrays cooperating to perform both pulse echo and through transmission ultrasonic testing on the fuselage stiffener.

20. The apparatus of claim 19, wherein the inner transducer array has a trapezoidal configuration of transducer to match the inner surface of the hat stiffener.

21. The apparatus of claim 19, wherein the outer and inner transducer arrays constitute a first group for scanning the cap and upper radius on one side of the hat stiffener; the apparatus further comprising a second group of outer and inner transducer arrays for scanning the cap and an upper radius on another side of the hat stiffener.

22. The apparatus of claim 19, further comprising equipment for processing pulse echo and through transmission data to locate anomalies in the part and using loss of back to distinguish low porosity from other anomalies.

* * * * *